United States Patent
Herrera Gómez et al.

(10) Patent No.: US 8,613,545 B2
(45) Date of Patent: Dec. 24, 2013

(54) SCAN ADIABATIC RESISTIVE CALORIMETER (SARC) WITH OHM HEATING IN THE SAMPLE

(75) Inventors: Alberto Herrera Gómez, Queretaro (MX); José Martín Yáñez Limón, Queretaro (MX); Guadalupe Barreiro Rodríguez, Queretaro (MX); Carlos Alberto Contreras Servín, Queretaro (MX)

(73) Assignee: Centro de Investigación y de Estudios Avanzados del Instituto Politécnico Nacional, San Pedro Zacatenco (MX)

( * ) Notice: Subject to any disclaimer, the term of this patent is extended or adjusted under 35 U.S.C. 154(b) by 824 days.

(21) Appl. No.: 12/808,302

(22) PCT Filed: Nov. 7, 2008

(86) PCT No.: PCT/IB2008/054656
§ 371 (c)(1),
(2), (4) Date: Jul. 22, 2010

(87) PCT Pub. No.: WO2009/112904
PCT Pub. Date: Sep. 17, 2009

(65) Prior Publication Data
US 2010/0296544 A1    Nov. 25, 2010

(30) Foreign Application Priority Data
Dec. 19, 2007 (MX) .................... MX/a/2007/016437

(51) Int. Cl.
*G01K 17/00* (2006.01)
*G01K 17/20* (2006.01)
*G01N 25/02* (2006.01)
*G01N 25/22* (2006.01)

(52) U.S. Cl.
USPC ............... 374/31; 374/25; 374/32; 374/36

(58) Field of Classification Search
USPC ......................... 374/31, 25, 36, 32
See application file for complete search history.

(56) References Cited

U.S. PATENT DOCUMENTS 4,130,016 A    12/1978   Walker
4,185,497 A    1/1980    Decker et al.
(Continued)

FOREIGN PATENT DOCUMENTS

DE    10259321 A1    7/2004
SU    1093913 A      5/1984

*Primary Examiner* — Andre J Allen
*Assistant Examiner* — Jamel Williams
(74) *Attorney, Agent, or Firm* — Rothwell, Figg, Ernst & Manbeck PC (57) ABSTRACT

The present invention describes a scan adiabatic resistive calorimeter (SARC) 1 with ohm heating of the sample 20, which measures the heating enthalpy and is formed of an inner cylinder 11 and a couple of pistons 15 and 16, thus forming said elements a cylindrical chamber hermetically closed 10, which avoids that during its operation can be material losses by leaks. Pistons 15 and 16 have, in one of their ends an electrode 31 and 36 respectively and they pass the electrical heating flow through the sample 20. In reference to this electric flow, the applied power is calculated and therefore, the supplied heat to the sample 20, which is equal to the specific enthalpy. To assure that the whole of the electric flow is conducted through the sample 20, the inner cylinder 11 is electrically isolated. The SARC 1 with ohm heating of the sample 20 is formed additionally of a spring with which the pressure of the experiment can be controlled and of instruments that include actuators 60, sensors and the necessary conditioning to make available in a computer 81, added to the calorimeter, the control objects and the controlled variables.

21 Claims, 8 Drawing Sheets

(56) References Cited

U.S. PATENT DOCUMENTS

| | | | |
|---|---|---|---|
| 4,428,684 A | * | 1/1984 | Kuraoka .......................... 374/25 |
| 4,500,214 A | * | 2/1985 | Calvet et al. .................... 374/36 |
| 4,765,749 A | * | 8/1988 | Bourgade et al. ............... 374/32 |
| 5,707,149 A | * | 1/1998 | Freire et al. .................... 374/33 |
| 7,012,820 B2 | | 3/2006 | Jitaru |
| 7,473,031 B2 | * | 1/2009 | Wolkin et al. ................... 374/31 |
| 2010/0296544 A1 | * | 11/2010 | Herrera Gomez et al. ..... 374/31 |

* cited by examiner

| Sample | Moisture amount | $c_P$ [J kg$^{-1}$ K$^{-1}$] | | | $k$ [W/mK] | |
|---|---|---|---|---|---|---|
| | | SARC | DSC | Sample in dry base | k (SARC) | k (Others) |
| Zeolite | 0.3 | 2100 ± 105 | 2100 ± 53 | 1123 | 0.58-0.0056* (T-25) | 0.58 |
| Bentonite | 0.58 | 2607 ± 40 | 2755 ± 71 | 875 | 1.1-0.0034 (T-25) | 0.90** |
| Bauxite | 0.19 | 1200 ± 54 | 1249 ± 31 | 795 | 0.71 | 0.91 |
| Hematite | 0.15 | 1100 ± 44 | 1150 ± 29 | 620 | 1.43 | 1.43 |
| Rice flour | 0.47 | 3100 ± 114 | 3001 ± 75 | 2000* | 0.46-0.0033 (T-25) | 0.4** |
| Corn flour | 0.58 | 2750 ± 15 | 2942 ± 74 | 1430* | 0.36-0.0037 (T-25) | 0.4 |
| Potato starch | 0.49 | 2800 ± 109 | 2808 ± 70 | 2000* | 0.40-0.012 (T-25) | --- |

\* $c_p$ values obtained with DSC in dry base.

\*\* $k$ values are obtained by the ratio $k = \alpha \rho c_p$. $\alpha$ is determined by photopyroelectrical techniques at environmental temperatures and $c_p$ by DSC.

FIGURE 9

SCAN ADIABATIC RESISTIVE CALORIMETER (SARC) WITH OHM HEATING IN THE SAMPLE

CROSS REFERENCE TO RELATED APPLICATION(S)

This application is a 35 U.S.C. §371 National Phase Entry Application from PCT/IB2008/054656, filed Nov. 7, 2008, and designating the United States. This application also claims the benefit of Mexican Patent Application No. MX/a/2007/016437 filed Dec. 19, 2007, the disclosure of which is incorporated herein in its entirety by reference.

FIELD OF THE INVENTION

The present invention is related to devices used to measure supplied or received heat quantities in a determined body and, more particularly with devices that measure the specific heat of samples such as plaster, wet minerals and some food systems in which the measurements are done by a heat scan of the sample by the Joule's effect and in adiabatic conditions.

BACKGROUND OF THE INVENTION

The development of measurement techniques to determine the thermal properties has been a very active area in the last decades. Lately the existing methods which use scan calorimeters suffer some deficiencies. For instance, in some devices it is necessary to use small samples with a large surface—volume ratio; in unstable solutions this produces the loss of volatile components during the placement of the sample. The present designs don't allow the use of large samples because the sample heating is made through the container's heating. This requires that the time for temperature is homogeneous in the sample; this factor is highly dependant on the sample's size. In some calorimeters the container is larger than the sample, which might produce a mass exchange between the sample and the empty space in the container. When the volatile components evaporate into the container's empty space, aside of introducing heat measuring errors, the balance of the chemical reactions can be affected, for example, diminishing the water contents or catalytic components in the sample.

In the presently known calorimeters, where the heat generation is internal, this might be done due to different phenomena such as chemical reactions, light absorption, sound absorption, particle absorption and electrical dissipation. The inwardly generated heat quantification is usually made by measuring the heat changes in the container, in this way, the transferred heat from the sample to the container is an effect integrated during the measurement, and these calorimeters require of this heat transference to work.

Among the documents that define the state of the art already mentioned there is the U.S. Pat. No. 4,130,016 in which it was divulged an adiabatic calorimeter designed to the high risk chemical research, particularly in studying the auto-heating reactions which can give situations of little control, wherein the reaction's recipient and the associated components in this device simulate closely the structure and the operation of a typical plant chemical reactor, finally this patent describes that the reaction's container is placed inside a metal cover and the whole unit is suspended in an isolated oven.

Another state of the art document which describes a calorimeter in which the heat is produced by light absorption is the U.S. Pat. No. 4,185,497 that describes a device to measure the energy absorption by the measurement material, wherein the temperature of the container in which the sample suspended is controlled, such container is a vacuum vase or deposit, the document also describes that the calibration is made by a known dissipation rate of the sample's energy. The sample is irradiated by a light beacon of a known power and the increase of the temperature in the sample is compared with the corresponding temperature increasing of the calibration sample. A method to scan the sample's heating is also provided. Another document, U.S. Pat. No. 4,765,749 exposes a calorimeter in which the generated heat inside the sample is made by the Joule's effect, more particularly, a calorimeter to measure energy transported by radiation and that have an external side exposed to the radiation and an inner side, said element experiences an increase in temperature during the interaction with the radiation and this temperature raising is measured by a thermo battery. Finally, the U.S. Pat. No. 7,012,820 B2 exposes and protects a calorimeter that seeks to obtain adiabatic conditions, in which the transferred heat from the sample to the container is calculated and the heating system is adjusted during the system's operation to compensate this heat loss.

From the technical knowledge obtained by the analysis of the above mentioned documents we can state that presently there is no resistive calorimeter which, starting with a scan can determine the specific heat of samples such as plaster, humid minerals and some food systems and, besides that, such heat quantity measurement process is made under adiabatic conditions.

Based in the mentioned above, we defined the following:

OBJECTIVES OF THE INVENTION

The first objective of this invention to supply a Scan Adiabatic Resistive Calorimeter with ohm heating of the sample (SARC) in which the sample is heated by the Joule's effect.

A second objective of this invention is to give a scan adiabatic resistive calorimeter with ohm sample heating to measure the calorific capacity of viscous and gel type materials.

A third objective of this invention is to give a scan adiabatic resistive calorimeter with ohm sample heating to measure the heat conductive ratio of viscous and gel type materials.

A fourth objective of this invention is to give a scan adiabatic resistive calorimeter with ohm sample heating wherein with independent heaters the heat exchange between the sample and its surroundings is minimized by using an automatic control.

A fifth objective of this invention is to give a scan adiabatic resistive calorimeter with ohm sample heating which for its operation mode does not require a calibration process, therefore it can be used as a primary method from the metrology's view.

These and other objective will be evident from the information presented here.

DETAIL DESCRIPTION OF THE INVENTION

The characteristic details of this scan adiabatic resistive calorimeter (SARC) with ohm heating of the sample are clearly shown in the following description and in the figures included, using the same reference signs to illustrate the same parts in the figures.

Figure 1:
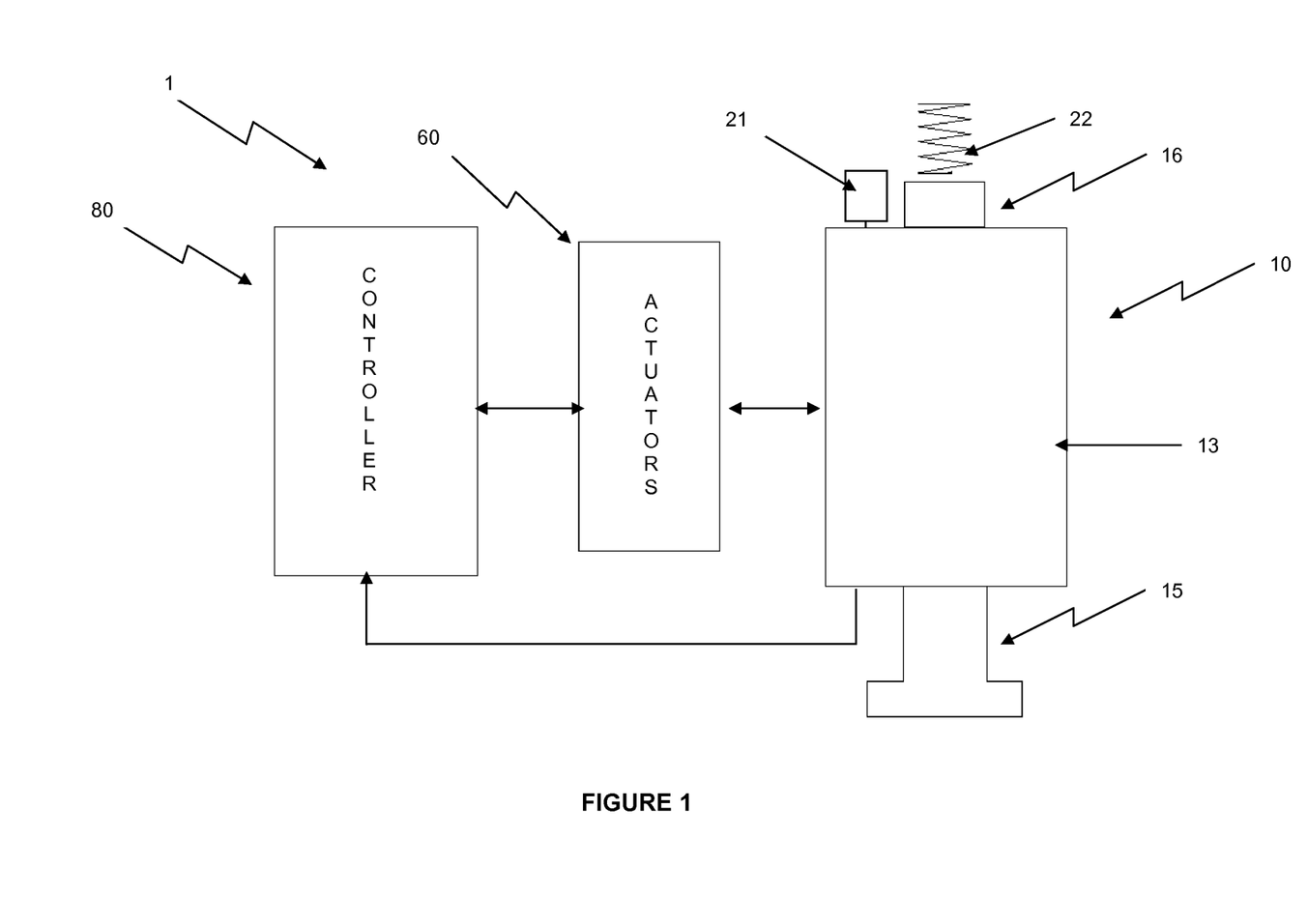
FIG. 1. Is a scheme diagram of a scan adiabatic resistive calorimeter with ohm sample of the present invention.

According to FIG. 1, the SARC 1 with ohm heating of the sample number 20 is made of a cylindrical chamber hermetically closed 10, a group of actuators 60 through which there is availability of both the control objects and the controlled variables, and a controlling system 80 which manipulates the control objects according the state of the controlled variables.

Figure 2:
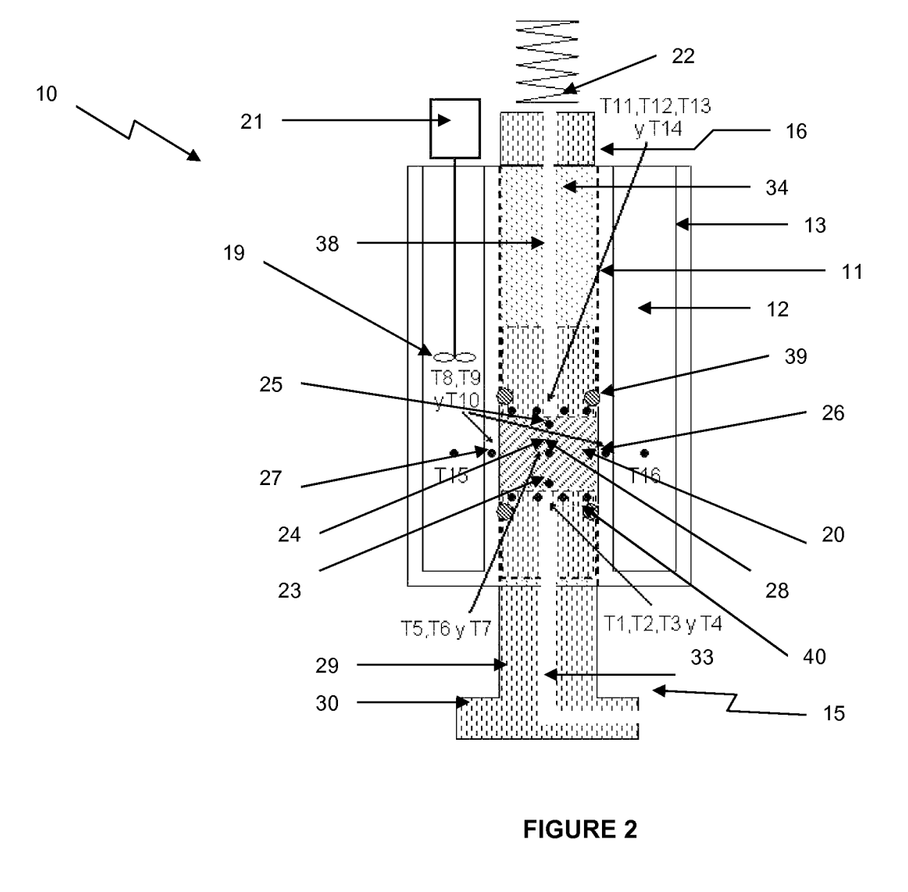
FIG. 2. Is a transversal cut of the hermetic cylindrical chamber of the calorimeter in FIG. 1.
Figure 3:
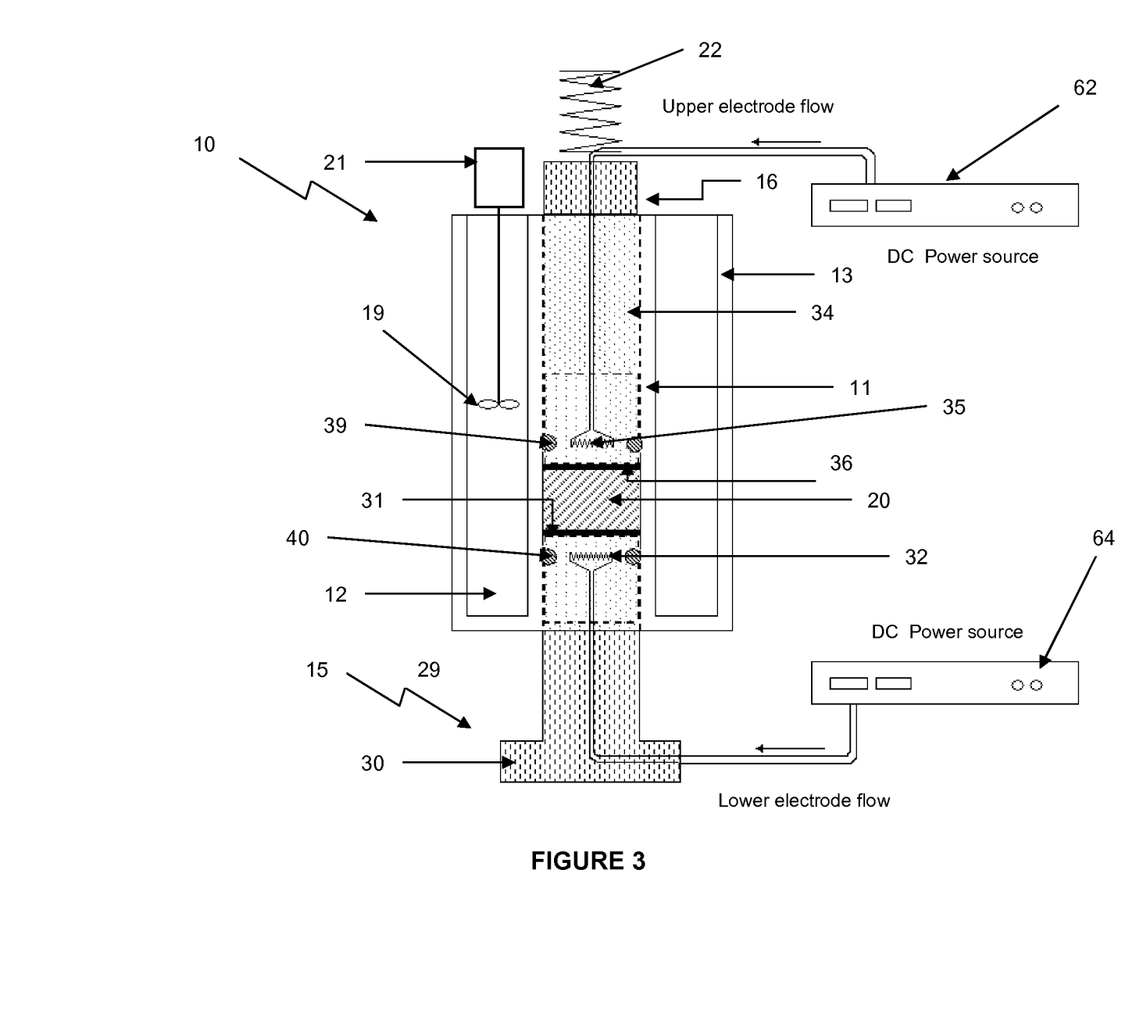
FIG. 3. Is a transversal cut of the hermetically closed cylindrical chamber of the calorimeter in FIG. 1, where the upper and lower pistons heating electrical resistors are visible as well as the electrical diagram for electrodes heating.
Figure 4:
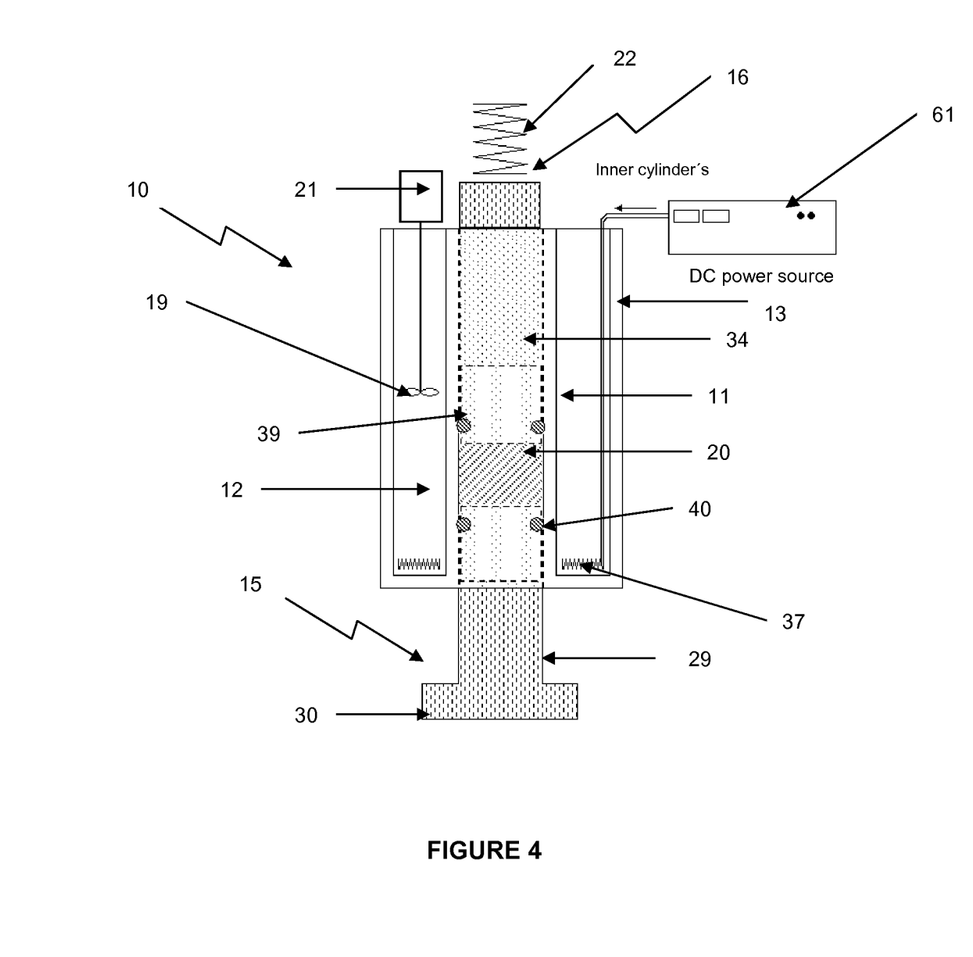
FIG. 4. Is a transversal cut of the hermetically closed cylindrical chamber of the calorimeter in FIG. 1, where the electrical resistor that heats the oil chamber and its electrical diagram for the wall heating.

As shown in FIGS. 2, 3 y 4, the hermetically closed cylindrical chamber 10 of the SARC 1 with ohm heating of the sample 20 has a concentric cylindrical form and it is formed from an outer cylinder 13 and an inner cylinder 11, a lower piston 15 and an upper piston 16, a helix 19 placed between the outer cylinder 13 and the inner one 11, said helix is coupled to an engine 21.

Within the inner cylinder 11 the sample 20 is contained, which is also contained between the upper and lower pistons 15 and 16, the inner cylinder is surrounded by a silicon oil chamber 12 in which two thermopars T15 and T16 are placed, those thermo pars record the oil temperature and a resistor 37 through which the oil chamber 12 is heated, this chamber is placed between the outer and the inner cylinders 13 and 11. In a preferred embodiment of the invention, the inner cylinder 11 is made of Teflon due to this is a very good electrical isolator, which is fundamental for the correct functioning of the calorimeter 1, because, being the inner cylinder in contact with the 15 and 16 pistons it becomes necessary that the electricity conducted through the inner cylinder equals zero, so ensuring that all the electricity passing from a first electrode 31 placed in the upper part of the lower cylinder 15 to a second one 36 placed in the lower part of the upper cylinder 16 will only pass through the sample 20, in the same fashion and due to the electrical isolation needed it is suggested that the outer cylinder 13 and the caps of the inner cylinder should be made of an isolating material (nylamid).

The lower piston 15 and the lower electrode 31 have a perforation 33 through which the thermopars T5, T6 and T7 that register the sample's 20 temperature in the points 23, 24 and 25 are introduced. The inner cylinder 11 additionally shows three compartments 26, 27 and 28 which form 120 degrees among themselves and where three more thermopars are placed T8, T9 and T10, which register the temperature on the inner cylinder's wall 11 between the oil and the sample.

The lower piston 15 is composed by a main body 29 and a base 30, both of circular section, which, in order to give stability and firm support to the lower piston 15 the base 30 has a bigger diameter than the section of the main body 29. In a preferred embodiment of the invention and to give the necessary electrical isolation, the main body 29 and the base 30 of the lower piston 15 are made of Teflon and the surface of the main body is made of aluminum and is used as an electrode 31.

In the inner part of the electrode 31 of the lower piston 15 four thermopars are placed T1, T2, T3 and T4 forming angles of 90 degrees among themselves to measure the corresponding temperature. The electrode 31 has an independent heating element that is a resistor 32 and the lower piston 15 has a cylindrical hole 33 in its center part through which thermo pars T1, T2, T3 and T4 pass as well as electrode's 31 feeding cables and the resistor 32. Thermo pars T1, T2, T3 and T4 register the electrode's 31 temperature.

The upper piston 16 is composed of a main body 34 of circular section, in a suggested mode of this invention alike the lower piston 15, the upper piston 16 is made of Teflon and the lower surface of the main body 34 is made of aluminum and is used as an electrode 36.

In the inner part of the electrode 36 of the upper piston 16 are placed tour thermopars T11, T12, T13 and T14 forming angles of 90 degrees among themselves to measure the corresponding temperature. This electrode 36 has an independent heating element which consists of a resistor 35 and, alike the lower piston 15, the upper piston 16 shows a circular hole 38 in its center part, through which the thermopars T11, T12, T13 and T14, the electrode's 36 feeding cables and the resistor 35 pass. Thermopars T11, T12, T13, and T14 register the electrode's 36 temperature.

Above the upper piston 16 is placed a device to control the pressure in the sample, this device contains a spring 22 which compression allows us to know the pressure applied to the sample.

In order to achieve a hermetic sealing in the upper and lower pistons 15 and 16 inside the inner cylinder 11 there have been placed beside the sample 20 of each one of the pistons 15 and 16 and in the back part of each one of the electrodes 36 and 31 of said pistons 16 and 15 adjusted o-ring seals 39 and 40.

Figure 5:
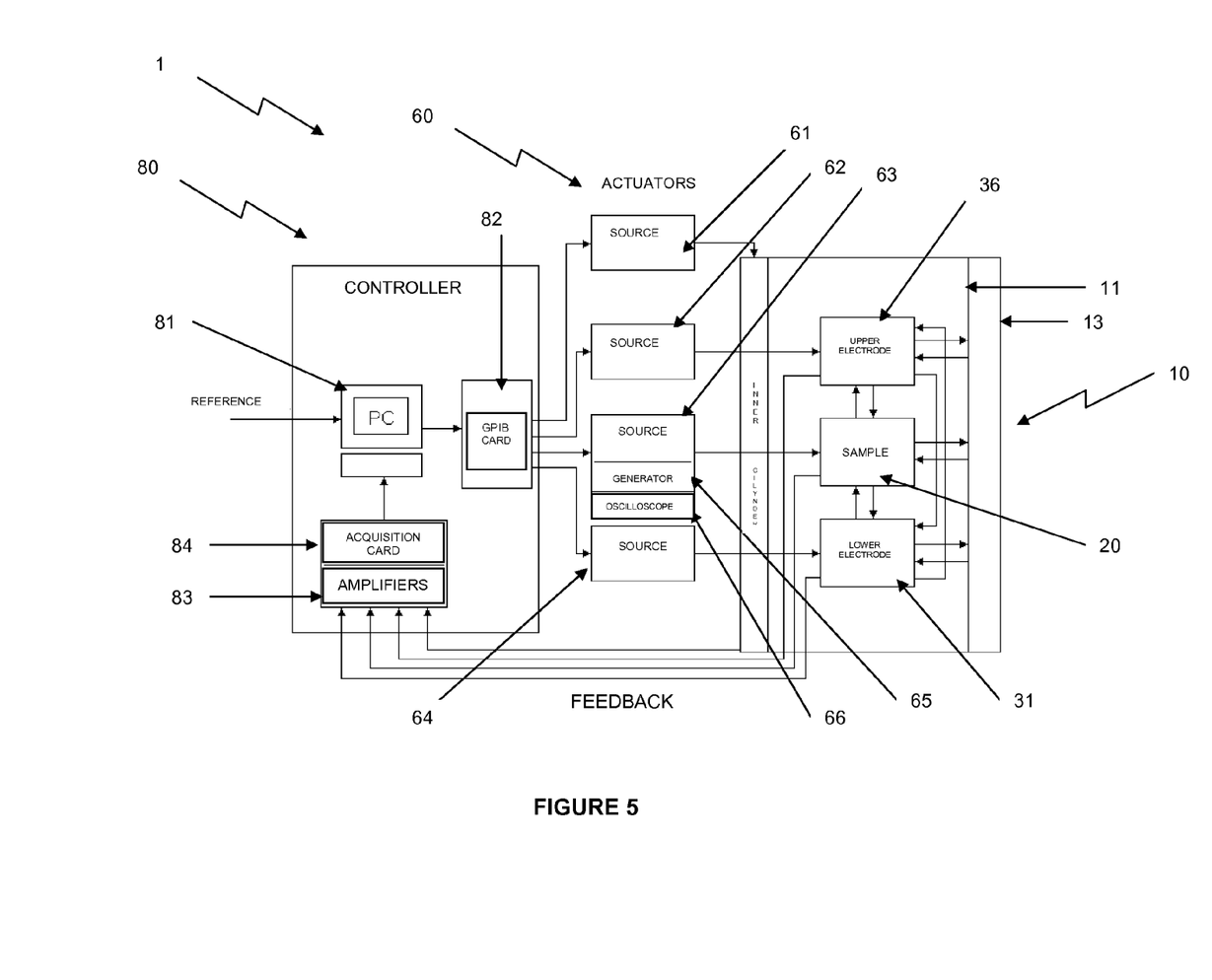
FIG. 5. Is a block diagram of the scan adiabatic resistive calorimeter with ohm heating according to the present invention.

Once detailed the elements that compose the cylindrical chamber hermetically closed 10 of the calorimeter 1, and based on the block diagram in FIG. 5, there will be described the way in which each one of the elements of the said chamber 10 interact with the group of actuators 60 and the controlling system 80 of the calorimeter 1.

The group of actuators 60 is composed of a primary DC power source 61, a secondary DC power source 62 a third AC power source 63, a fourth DC power source 64, all of them independent, a signal generator 65 and an oscilloscope 66.

The reason for the four independent power sources 61, 62, 63 and 64 is due to the fact that each one of the elements to which each one is connected have a different dynamic and therefore, the speed in which they can be heated is also different, so, considering that the objective is that every one of them heats at the same time so the results obtained are true, the heating speed of the system's heating is limited to the heating speed of the slowest element, in this case, the upper electrode 36 of the upper piston 16.

The first power source 61 makes flow an electrical current through the resistor 37, suspended in the mineral oil of the chamber 12 as shown in FIG. 4 to transfer heat by means of dissipation, where, to heat the whole oil chamber the helix 19 connected to the engine 21 is used and thus seized the convection flows, in this case, the heating of the inner cylinder 11 is made by heat conduction and such heat is transmitted to the simple 20 through the walls of the inner cylinder 11 and shows a diffusion retardation which is seized to average the gradients that the oil had due to the convection flows, thus achieving a more uniform temperature on the border of the inner cylinder's 11 wall which is in contact with the sample 20.

The second power source 62 is connected to the upper electrode 36 of the upper piston 16, while the fourth power source 64 is connected to the lower electrode 31 of the lower piston 15, as shown in FIG. 3, in such way that the second and the fourth power sources 62 and 64 conduct the electric current through the resistors 35 and 32 respectively, in order to generate heat by dissipation, in such way that the heating of the pistons 15 and 16 is made by heat conduction. Each of the electric resistors 35 and 32 are in contact with the piston by the means of a refractory heat conductive cement, wherein the refractory cement makes contact with the whole available surface molding itself to the shape of both the resistors 35 and 32 and the pistons 16 and 15, thus displacing any air bubble which could be formed between both elements (resistors 35 and 32 and pistons 16 and 15) maximizing the heat conduction of the resistors 35 and 32 to the pistons 16 and 15.

Figure 6:
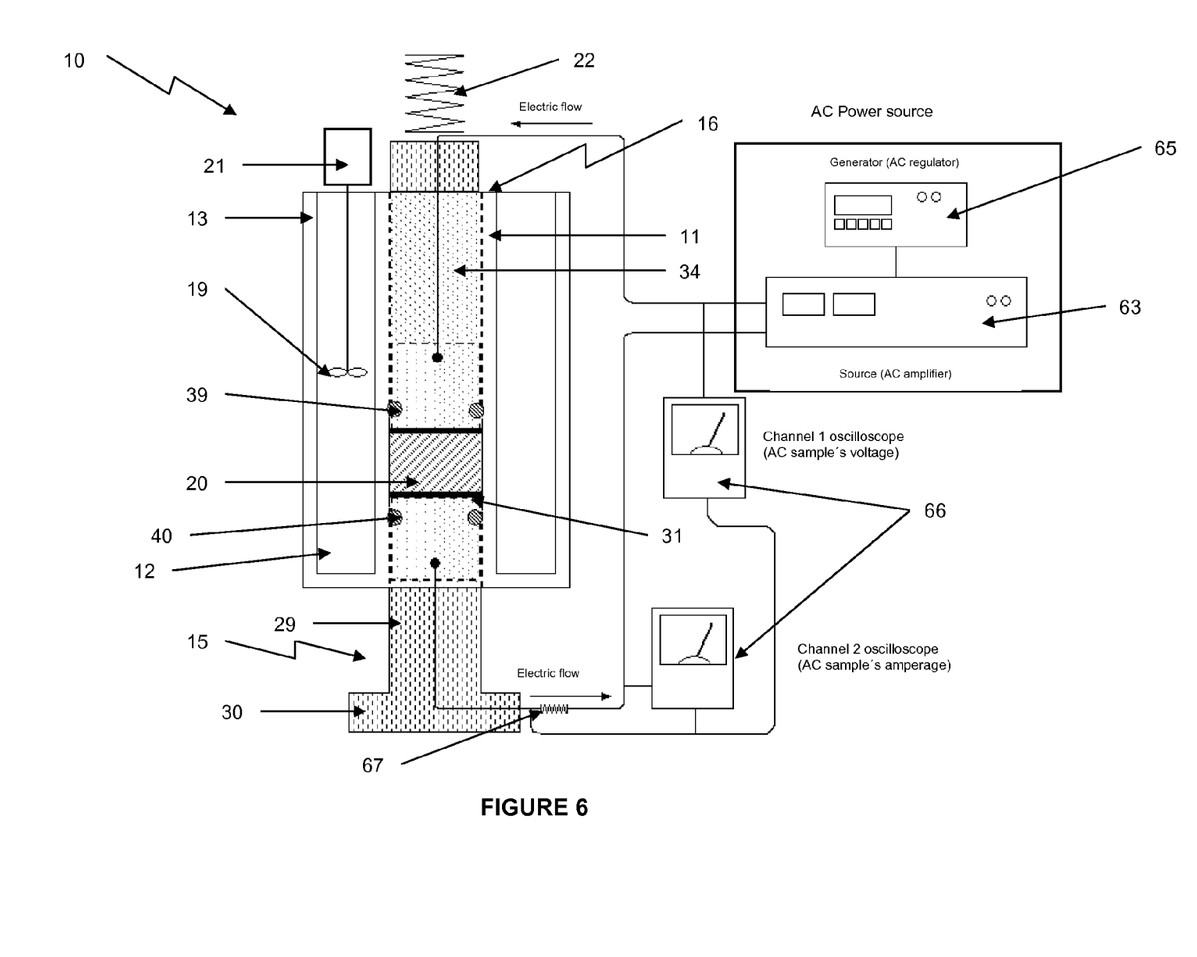
FIG. 6. Is a transversal cut of the hermetically closed cylindrical chamber of the calorimeter in FIG. 1 is shown in which is also shown the electrical diagram for the ohm sample heating and the measurement of the electrical variables.

The power necessary to heat the sample 20 is supplied by the third power source 63 which is an AC power source controlled in voltage and in a signal generator 65 that supply the reference signal frequency and amplitude desired to apply to the sample 20. The aforementioned is shown in FIG. 6.

On other side, the calorimeter's 1 control system 80 is composed by a personal computer 81, an 8 bit interphase parallel communication card that supports transference rates up to 1 Mbyte/s known as GPIB 82, amplifiers 83, a data acquisition card 84 and a software which allows to manipulate the acquired data. This controlling system 80 is through which data are acquired, the power sources 61, 62, 63 and 64 are controlled, the temperature increment is registered in the 16 points within the hermetically closed cylindrical chamber 10 and is registered the power dissipation in the sample.

The power sources 61, 62, 63 y 64, as well as the signal generator 65 and the oscilloscope 66 are connected to the GPIB card 82, since it is through this card that the communication of said actuator elements and the controlling system 80 is done.

From the integration and co-relation of each one of the three main elements that compose the SARC 1 with ohm heating of the sample, that is, the hermetically closed cylindrical chamber 10, the group of actuators 60 and the controlling system 80 we can proceed to measure the electrical variables.

To measure the electrical variables of the sample it is used the oscilloscope 66 which converts the AC and voltage signals into a root mean square value (RMS) and allows verifying that the current and the voltage are in phase.

The RMS values are stored in the personal computer 81 in order to make the calculations for the power applied to the sample.

The voltage is directly measured from the power source's 63 terminals, while to measure the current is necessary to place a resistor 67 of low value and power to make a voltage—current Ohm's law conversion.

To measure the electrical variables of the upper and lower pistons 16 and 15 and those of the inner cylinder 11 we use the gauges included in each power source 61, 62 and 64 and those values are retrieved by the GPIB card 82 COM link.

Finally, the temperature in the cylindrical chamber 10 is monitored in 16 representative points, that is, in each of the T1-T16 thermopars placed in the chamber 10, said temperature is registered through an analogical signal conditioner 83, in which the signal is amplified and sent to a data acquisition card 84, which in its turn sends the acquired information to the computer 81 and thus, close the manipulation cycle of the control objects by the state of the controlled variables.

Suggested Method to Carry out the Invention

The sample 20 with viscosity of plaster or gel type is placed inside the inner cylinder 11 and the pistons 15 and 16. To place the sample 20, the lower piston 15 is kept fixed and the inner cylinder 11 slides until there is a width between the lower electrode 31 and the upper part of the inner cylinder 11 of two centimeters. In this position the previously weighted sample 20 is placed up to the border in the same inner cylinder 11, immediately the upper piston 16 is placed this piston contains the upper electrode 36 and is pressed to eliminate the air that the sample 20 could contain, immediately the inner cylinder 11 slides upwards, with the system lower piston 15—sample 20—upper piston 16 as sliding axis until the preset levels are met, in such manner that the sample 20 is always in the center of the inner cylinder 11 and taking care that the thermopars T5, T6 and T7 which monitor the temperature of the sample 20 do not bend. Finally there is made a minimum adjustment with a fixed press placed in the upper part of the chamber 10 that presses the sample 20 through the upper piston 16 and verifying that the resistance of the sample 20 is within the range of KΩ units, which indicates a good electrical contact in the studied samples 20.

The placement of the sample 20 is done in such way that guarantees the filling of all the space set for the sample 20, avoiding the possibility of bubbles. This is an important feature, because assuring that the sample 20 occupies all the available volume, it is also assured an electrical continuity and homogeneity in the electrical power dissipation. For this reason, the calorimeter 1 can be applied in viscous or liquid samples that don't suffer a phase transition to gas state within the range of measurement temperature.

Since the sample 20 is placed and sealed, the pressure can be increased to the desired value without loss of material. The upper piston 16 is mobile, so the pressure can be kept constantly even when the sample 20 expands due to the temperature increment or the sample's 20 structural changes. It is important to emphasize that, differently from the conventional calorimeters, in this way is possible to set constant pressure conditions, at the same time avoiding the materials evaporation using highly enough pressure.

An AC voltage is applied to electrodes 31 and 36 allowing the sample 20 is heated by electrical dissipation; such dissipation is uniform in homogeneous samples. The calorimeter 1 uses high precision with which the dissipated electrical power in the sample 20 can be measured.

An important advantage of the calorimeter 1 is that does not require calibration, therefore can be used as a primary system from the metrological view. The upper piston 16 can be moved to allow the free expansion of the sample 20 during the operation. The pressure is kept constant during the calorimeter's 1 operation by means of an external device, in such way that the heat input in the sample 20 equals the enthalpy change rate, thus the specific enthalpy can be measured by the calorimeter 1.

The heat exchange with the surroundings is minimized, keeping the sample's 20 surroundings temperature the closest possible to the sample's temperature, using independent heating elements in the zone of each electrode 31 and 36 and in the zone of the inner cylinder's 11 surrounding oil which contains the sample 20, for this, it is used a differential integral proportional automatic control (PID) or an ad hoc advanced control.

Additionally, the heat exchange between the sample 20 and its surroundings is determined by numeric calculations, solving the heat diffusion equation, with the dissipated power in the sample 20 as a heat source and the experimental temperature evolution in the oil zone and the electrode heaters 31 and 36 are used as border conditions.

Following it is described the SARC's with ohm heating of the sample 20 functioning.

The calorific capacity is obtained by using the following expression:

$$c_p = \frac{P + \frac{dQ}{dt}}{m \frac{dT}{dt}} \qquad \text{Eq. 1}$$

Where P is the dissipated power in the sample 20, m is the sample's 20 mass, and dT/dt is the temporal derivate of the sample's 20 temperature, dQ/dt is the gained heat ratio (or lost if it's negative) by the sample 20, by the means of the heat transference through its borders. The heat can flow from the surroundings to the sample 20 and vice versa due to the electrodes 31 and 36 and the inner cylinder 11 are heated independently. When the sample 20 is heated more slowly than its surroundings, dQ/dt is possitive, and is negative when the temperature of the sample 20 is greater and loses heat to the surroundings; dQ/dt is given by the following expression:

$$\frac{dQ}{dt} \equiv -\int_S J \cdot n \, dS \qquad \text{Eq. 2}$$

Where S is the surface defined by the sample's container, J, is the heat flow and n is the sample's 20 surface's normal. The expression given in Eq. 1 can be contrasted with the expression used in the differential scan calorimetry's direct method, in which the calorific capacity is obtained by using the expression $c_p=(dQ/dt)/(mdT/dt)$. In the case of our calorimeter 1 the main heat source is the dissipated power in the sample 20 by Joule's effect (P) and the term dQ/dt is minimized. Under ideal operating conditions of the calorimeter 1 the term dQ/dt must equal zero. A great advantage of the calorimeter with ohm heating in the sample 20 is that it becomes possible to estimate precisely the applied power, P=IV, which is the most important term in Eq. 1. The second term, dQ/dt is reduced to small values by using an automatic control based on the modification of a basic PID control; the factor dT/dt is evaluated by numerical differentiation in the sample's temperature.

The term dQ/dt is calculated by numerical means. The heat diffusion equation is solved by numerical, using the finite element. The border conditions are obtained from the temperature's experimental values registered in the oil and in the electrodes' 31 and 36 zone. The numerical solution allows the time evolution of the temperature in the sample 20 and its surroundings (electrodes 31 and 36 and in the inner cylinder's 11 wall). The term dQ/dt is determined from the temperature's numerical solution, solving the Eq. 2's integral for each sample 20 under measurement. These calculations involve the previous knowledge of the calorimeter's 1 building material's specific heat and the thermal conductivity and the thermal conductivity of the sample 20. This calorimeter 1 is also appropriate to determine the thermal conductivity of the sample 20 as is described next.

The thermal conductivity of the sample 20 can be obtained by heating one of the elements in the chamber 10 (upper electrode 36) and analyzing the sample's 20 temperature evolution and in the other elements (lower electrode 31 and the inner cylinder's wall 11). The quickness in which the lower electrode 31 heats directly depends on the thermal conductivity and the calorific capacity of the sample 20. Therefore, the calculation of the sample's 20 thermal conductivity is linked to the term dQ/dt in calculating the calorific capacity and vice versa. This is why both experiments are analyzed simultaneously.

In the calorific capacity measurement experiment, all elements are heated at the same time to avoid heat transference from the sample 20 to its surroundings, and in the experiment to measure the thermal conductivity, the upper electrode 36 is heated and the heat is transferred through the sample 20 to the lower electrode 31 and the inner cylinder's 11 wall.

The assembled system's analysis is stable and converges quickly. This is because only the term dQ/dt in evaluating the calorific capacity is coupled with the thermal conductivity evaluation. Joule's dissipation term (P in Eq. 1) is the most important to determine the calorific capacity and is completely uncoupled, therefore this term itself supplies a very fine first approach to determine the calorific capacity through temperature. While in the thermal conductivity it is proposed a linear variation with temperature in the studied temperature range. The calorific capacity is determined for each measured temperature.

The error involved in the $c_p$ estimation was determined from the uncertainty of the main variables which affect directly or indirectly the $c_p$ calculation according to Eq. 1

These variables are the dissipated power in the sample, temperature, mass and the incoming or outgoing heat of the sample during the measurement. The expression for the uncertainty obtained is:

$$\Delta C_p = C_p \left( \frac{\Delta P}{P + \frac{dQ}{dt}} + \frac{\Delta m}{m} + \frac{\Delta\left(\frac{dQ}{dt}\right)}{P + \frac{dQ}{dt}} \right) \qquad \text{Eq. 3}$$

Where ΔP is the uncertainty in the applied power, Δm is the uncertainty of the mass and ΔdQ/dt is the uncertainty in the added or lost heat esteemed in the sample through its borders. The first two terms' contribution is much smaller than the one associated with ΔdQ/dt. This term is numerically esteemed by calculations of finite elements. The uncertainty arises mainly from the temperature difference ΔT, between the experimental temperatures and the temperatures numerically reproduced in the sample.

To show the operation of the SARC 1 with ohm heating of the sample 20 we propose two examples representing organic and inorganic materials, in which the $c_p$ is determined, using the calorimeter 1, those materials are: a) Bentonite ($Al_2O_3 4SiO_2H_2O$) with 0.0457 kg of water up to 42% in weight and b) Corn flour with 0.050 kg of water up to 42% in weight.

The sample's volume is determined by the pistons' position, which is close to 32 $cm^3$, the sample's mass is determined at the end of the measurement process. The experiment consists in a temperature scanning from environment's temperature (approximately 25° C.) up to 75° C. a in a heat increment rate of 4° C./min. For comparative reasons, the sample's $c_p$ was also measured under the same preparing conditions, using a market's differential scan calorimeter (DSC). The pressure is kept constant and very close to the atmospheric pressure by using an external device.

Figure 7:
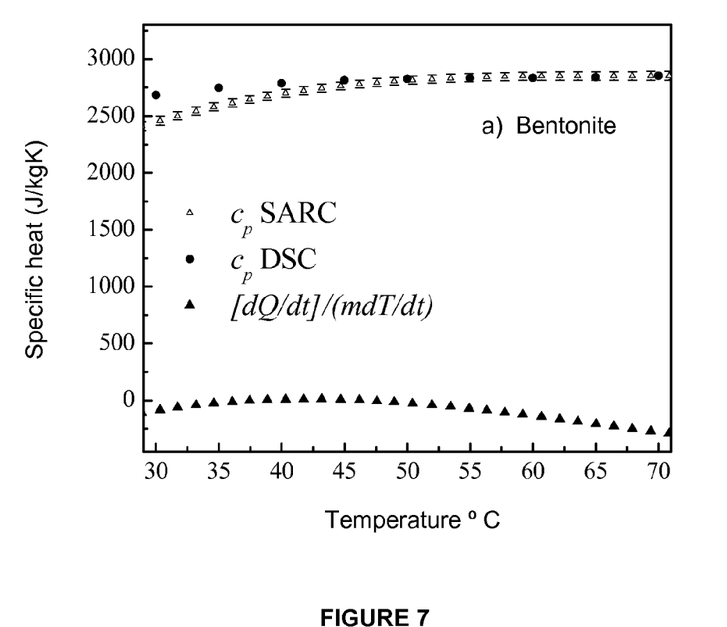
FIG. 7. Shows a result graphic where, in a bentonite sample the Cp is determined using the calorimeter in FIG. 1 and DSC commercial equipment.

The method to calculate the calorific capacity of the samples has been formerly described. The graphic in FIG. 7 shows the results for the bentonite sample, the $c_p$ values increase from 2478 J/kgK at 31° C. to 2855 J/kgK at 70° C., the error margin is close to a 2%. The difference with the values obtained with the DSC was close to 6% at 30° C., for higher temperatures the difference diminished and above 45° C. the DSC's values and those of the calorimeter 1 were within our calorimeter's 1 error margin.

Using the automatic control the contribution due to the heat exchange between the simple and its surroundings was substantially reduced (the term dQ/dt is small). However, the finite element calculations allowed to calculate in a right way the contributions of this heat exchange and to add them to the $c_p$ determination.

Figure 8:
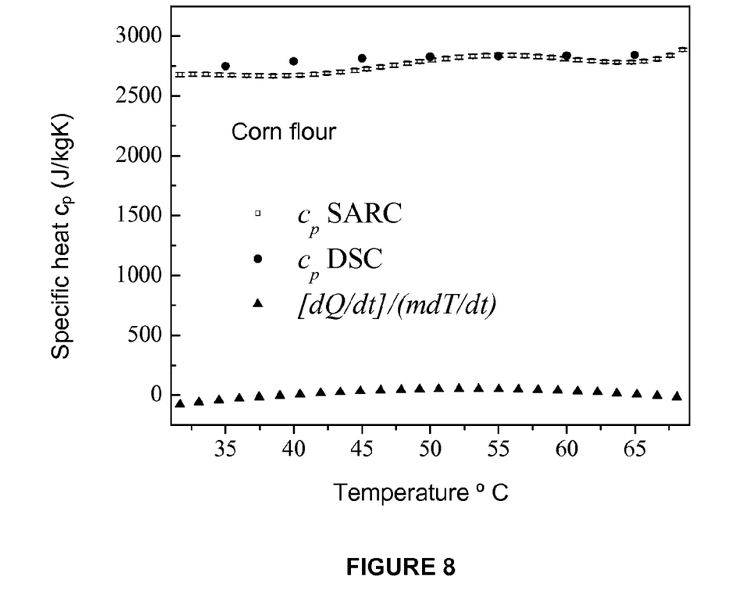
FIG. 8. Shows a result graphic where, in a corn flour sample the Cp is determined using the calorimeter in FIG. 1 and DSC commercial equipment.

FIG. 8 shows the results for a corn flour sample. The different elements' temperature in the calorimeter 1 kept close to them, in such way that the term dQ/dt contribution was very small and thus the uncertainty in the measurement was very small. Given that most of the sample's absorbed heat comes from electrical dissipation, which can be measured with enough accuracy, this allows us to conclude that the $c_p$ results are quite precise, with uncertainty rates under 2% as the error margin shows in these measurements. The maximum difference with the results obtained by the DSC is close to a 4% at 40° C., for the rest of the temperatures measured, the difference between the DSC and the calorimeter 1 is smaller.

Figure 9:
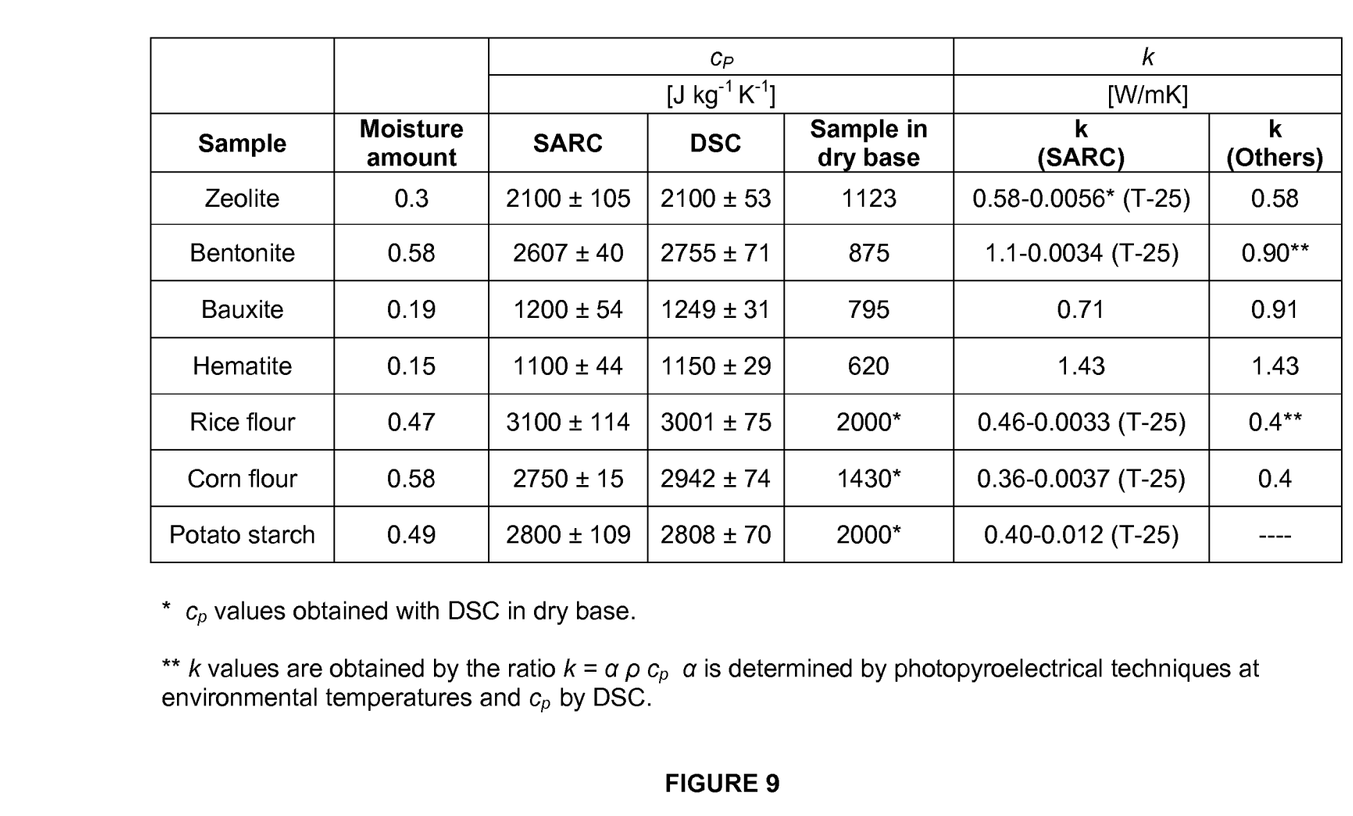
FIG. 9. Shows a Cp value table obtained in a temperature of 35° C. by the calorimeter shown in FIG. 1 and the DSC commercial equipment with different samples.

In FIG. 9 it is shown a table with $c_p$ values obtained at 35° C. using the calorimeter 1 and the market's DSC equipment in Zeolite, Bentonite, Bauxite, Hematite, rice flour, corn flour and potato flour samples. There are also included $c_p$ values of these materials in dry base, as well as the thermal conductivity versus temperature values obtained with the calorimeter 1, which are approximately constant for the mineral samples and the organic samples show a decreasing behavior with temperature. The thermal conductivity values obtained with the calorimeter 1 are close to the dry base values registered in the literature.

The invention claimed is:

1. A scan adiabatic resistive calorimeter (SARC) with ohm heating of the sample of the type that beginning with a scan heating of plaster, wet minerals and some food system samples, in adiabatic conditions and in constant pressure is determined the specific heat and the thermal conductivity in said sample, comprising a cylindrical chamber hermetically closed which is formed of an outer and an inner cylinder, in such manner that between the outer and the inner cylinders there forms a chamber which is filled with mineral oil, inside said oil filled chamber there are a resistor connected to a power source to heat the oil and a helix joined to an engine that helps to dissipate the heat given by the resistor in the whole oil chamber, wherein both the temperature in the inner cylinder and that of the oil chamber are continuously monitored by thermopars which are placed inside the inner cylinder and the oil chamber, the cylindrical chamber is also formed by a lower and an upper piston which are placed inside the inner cylinder and those are supplied in the end that is in contact with the sample with electrodes connected to two resistors, these resistors are fed by independent power sources, and placing in the inner part of both electrodes thermopars which monitor their temperature, in such way that there forms a free space within the inner cylinder which is monitored by thermopars and between the upper and lower pistons the sample can be placed and connected through the electrodes to a power source and a signal generator, the calorimeter is also composed by a section of actuators which is formed of the power sources connected to the resistors in the oil chamber, the upper piston, the lower piston and the sample, as well as an oscilloscope and the signal generator; and finally the controlling system which manipulates a set of control objects respecting a set of controlled variables' state which is composed by a personal computer, a GPIB phase COM link card, amplifiers and a data reception card, all connected among themselves and with the actuators and the elements that compose the cylindrical chamber hermetically closed.

2. The scan adiabatic resistive calorimeter (SARC) with ohm heating of the sample, according to claim 1, wherein said thermopars used to monitor the temperature in the inner cylinder wall between the oil and the sample are three in number and are placed circularly forming angles of 120 degrees among themselves.

3. The scan adiabatic resistive calorimeter (SARC) with ohm heating of the sample, according to claim 1, wherein said inner cylinder comprises three thermopars that monitor the sample's temperature, which are placed and aligned in the space where the sample is placed.

4. The scan adiabatic resistive calorimeter (SARC) with ohm heating of the sample, according to claim 1, wherein said oil chamber which surrounds the inner cylinder comprises two thermopars that register the oil temperature.

5. The scan adiabatic resistive calorimeter (SARC) with ohm heating of the sample, according to claim 1, wherein in a preferred embodiment of this invention said mineral oil that fills the oil chamber that surrounds the inner cylinder is silicon oil.

6. The scan adiabatic resistive calorimeter (SARC) with ohm heating of the sample, according to claim 1, wherein in a preferred embodiment of this invention said outer cylinder is made of nylamid.

7. The scan adiabatic resistive calorimeter (SARC) with ohm heating of the sample, according to claim 6, wherein in a preferred embodiment of this invention said inner cylinder is made of Teflon.

8. The scan adiabatic resistive calorimeter (SARC) with ohm heating of the sample, according to claim 1, wherein said lower piston is formed of a main body and a base, both of circular section, where, in order to give stability and firm support to the piston, the base is of greater diameter than the main body's section, both, the base and the main body show a cylindrical hole in its central part, through which the thermopars, the feeding cables and the resistors connected to them pass.

9. The scan adiabatic resistive calorimeter (SARC) with ohm heating of the sample, according to claim 8, wherein in a preferred embodiment of this invention and in order to achieve the necessary isolation, the main body and the base of said lower piston are made of Teflon.

10. The scan adiabatic resistive calorimeter (SARC) with ohm heating of the sample, according to claim 8, wherein the surface of said main body of the lower piston is made of aluminum and is used as an electrode in which lower part and forming an angle of 90 degrees among them there are placed four thermopars to measure the corresponding temperature.

11. The scan adiabatic resistive calorimeter (SARC) with ohm heating of the sample, according to claim 1, wherein said upper piston is composed of a main body of circular section, showing a cylindrical hole in its central part, through which thermopars, electrode's feeding cables and a resistors to which is connected pass.

12. The scan adiabatic resistive calorimeter (SARC) with ohm heating of the sample, according to claim 11, wherein in a preferred embodiment of this invention and in order to achieve the necessary isolation, said upper piston is made of Teflon.

13. The scan adiabatic resistive calorimeter (SARC) with ohm heating of the sample, according to claim 11, wherein the lower surface of said upper piston's main body is made of aluminum and is used as an electrode that in its inner part and forming angles of 90° among themselves there are placed four thermopars to measure the corresponding temperature.

14. The scan adiabatic resistive calorimeter (SARC) with ohm heating of the sample, according to claim 11, wherein on said upper piston it is placed a device to control the pressure in the sample, this device contains a spring which compression allows us to know the pressure applied to the sample.

15. The scan adiabatic resistive calorimeter (SARC) with ohm heating of the sample, according to claim 1, wherein each one of said electric resistors that are placed in the upper and lower pistons are in contact with those by means of a refractory heat conducting cement.

16. The scan adiabatic resistive calorimeter (SARC) with ohm heating of the sample, according to claim 1, wherein in order to achieve a hermetic closing of said upper and lower pistons inside the inner cylinder there have been placed in the parts surrounding the sample on the pistons on the back part of each one of the electrodes of the said pistons seals of o-ring type.

17. The scan adiabatic resistive calorimeter (SARC) with ohm heating of the sample, according to claim 1, wherein the AC power source and the signal generator connected to said sample supply the frequency and amplitude of the reference signal wished to apply to the said sample.

18. The scan adiabatic resistive calorimeter (SARC) with ohm heating of the sample, according to claim 1, wherein the power sources of said actuators section which are connected to the oil chamber's resistors, the lower and upper pistons are DC power sources.

19. The scan adiabatic resistive calorimeter (SARC) with ohm heating of the sample, according to claim 1, wherein said power sources of the actuators section which are connected to the sample, are AC power sources.

20. The scan adiabatic resistive calorimeter (SARC) with ohm heating of the sample, according to claim 1, wherein the information that the computer receives from said power sources, as well as from the oscilloscope's and the signal generator's is received through a GPIB COM link card.

21. The scan adiabatic resistive calorimeter (SARC) with ohm heating of the sample, according to claim 1, wherein the information that the computer receives about the temperatures registered by said thermopars is received through signal amplifiers and a data acquisition card.

* * * * *